United States Patent [19]

Corliss

[11] Plant 4,757

[45] Aug. 11, 1981

[54] EUONYMUS PLANT—CORMAST VARIETY

[75] Inventor: Clifford D. Corliss, Ipswich, Mass.

[73] Assignee: The Conard-Pyle Company, West Grove, Pa.

[21] Appl. No.: 150,962

[22] Filed: May 19, 1980

[51] Int. Cl.[3] ..... A01H 5/12

[52] U.S. Cl. ..... Plt./63

[58] Field of Search ..... Plt./63

*Primary Examiner*—Robert E. Bagwill

*Attorney, Agent, or Firm*—Burns, Doane, Swecker & Mathis

[57] ABSTRACT

A new and distinct variety of *Euonymus fortunei* which is a branch mutation of the Emerald'N Gold variety (i.e., U.S. Plant Pat. No. 2,231) is provided. The new variety possesses smaller leaves than the parent variety which are slightly more elliptic in shape and attractively variegated in color. More specifically, the mature leaves are dark green and have light to medium yellow margins. The new variety is shorter and more spreading than the parent and can be characterized as having a distinctly dwarf growth habit which renders it highly suited for use as a semi-prostrate ground cover.

2 Drawing Figures

SUMMARY OF THE INVENTION

The new variety was discovered and selected by me during 1973 while present in a cultivated block of plants of the Emerald'N Gold variety (U.S. Plant Pat. No. 2,231) of *Euonymus fortunei* being grown under my direction at the nursery property of Corliss Bros., Inc. at Ipswich, Mass. A distinctive branch of a single plant was discovered having a growth habit, leaf size and leaf appearance which differed from that of the Emerald'N Gold variety. This branch was preserved and continued close observation has confirmed its distinctive characteristics which differ from all varieties of *Euonymus fortunei* of which I am aware.

The following combination of characteristics is exhibited by the new variety:

(a) a distinctly dwarf habit of growth rendering the plant suitable for use as a semi-prostrate ground cover, (b) smaller variegated leaves which when mature are dark green with light to medium yellow margins, (c) vigorous growth characteristics, (d) the ability to thrive under a wide range of climatic conditions, and (e) the ability to be sheared within prescribed limits or shaped to a specific form.

Asexual reproduction of my new variety by cuttings has been accomplished at Ipswich, Mass. and West Grove, Pa. Such propagation through at least six generations has demonstrated that the unique combination of characteristics has been established and is transmitted to successive generations.

The new variety has been named the Cormast variety.

BRIEF DESCRIPTION OF THE PHOTOGRAPHS

The accompanying photographs show a typical specimen of the new variety as depicted in color as true as reasonably possible to make the same in a color illustration of this character. The photographs were made during mid-summer of a representative plant and plant parts thereof two growing seasons following the year of propagation. The subject plant was grown at West Grove, Pa. in an artificial soilless medium.

FIG. 1 illustrates the appearance of a representative plant of the new variety, and FIG. 2 illustrates representative branches of the new variety as well as the appearance of the upper and under surfaces of typical leaves.

DETAILED DESCRIPTION

Figure 1:
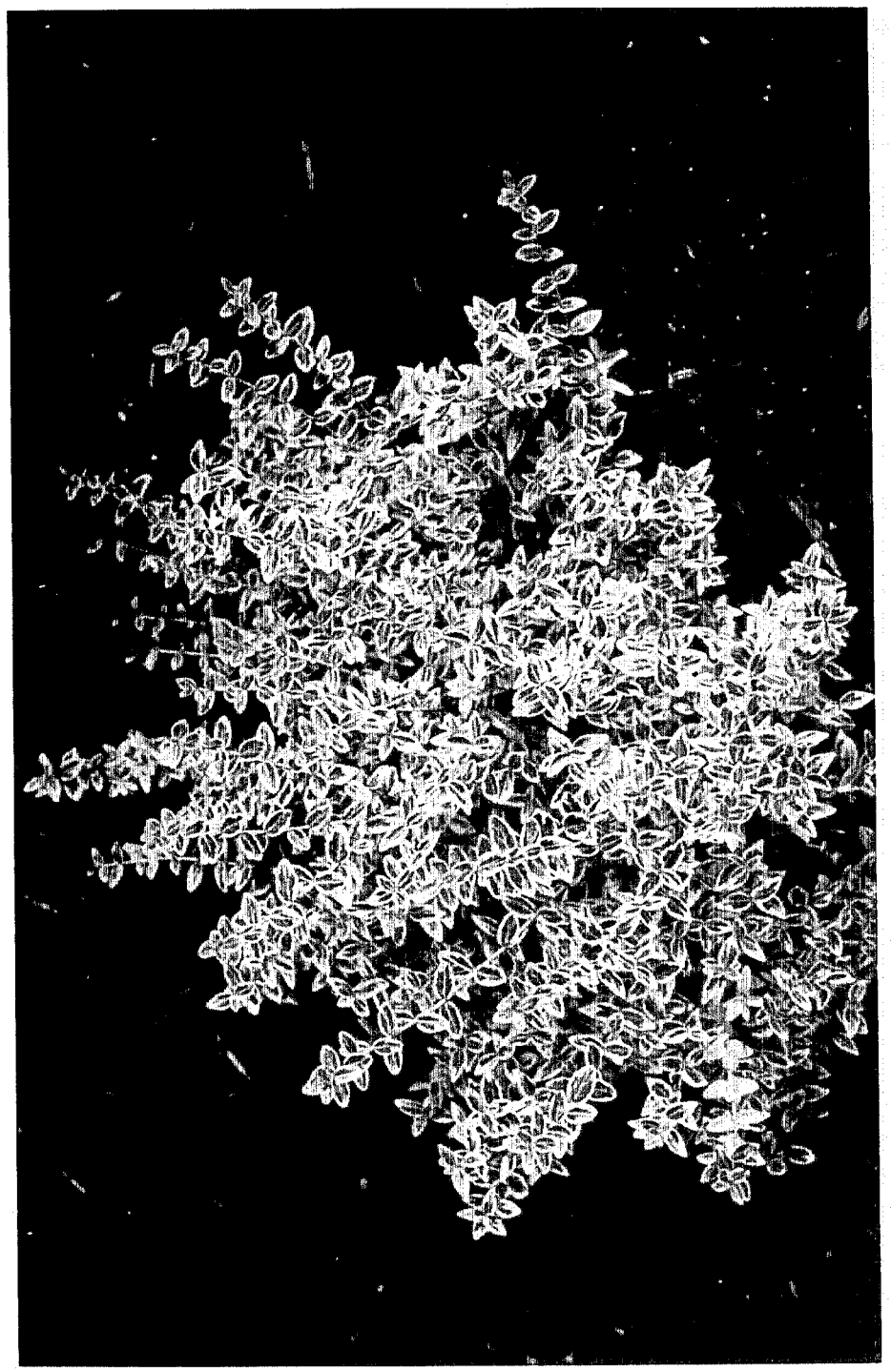
Figure 2:
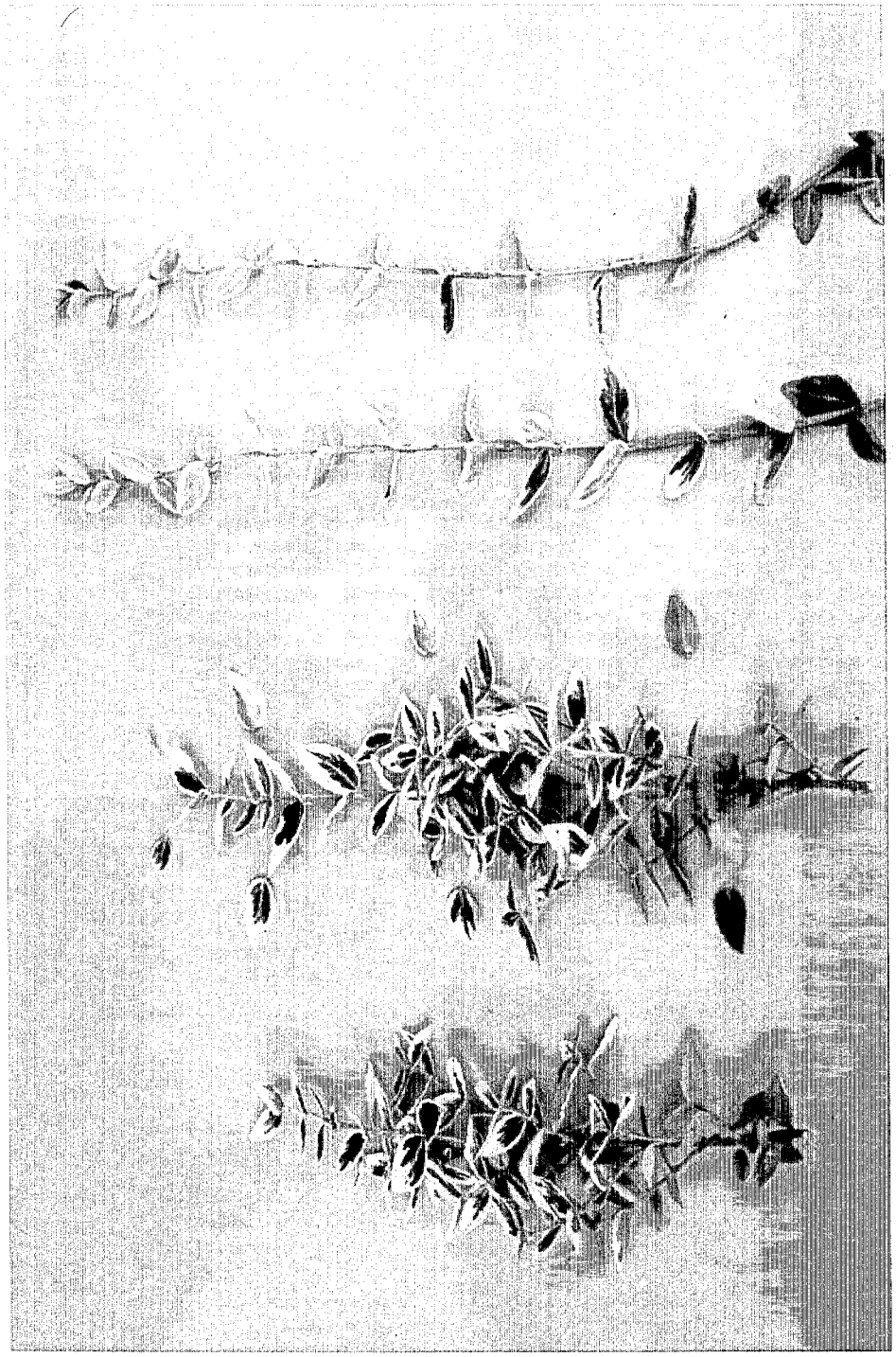

The following is a detailed description of my new variety, with color terminology in accordance with the R.H.S. Colour Chart of the Royal Horticultural Society, London, England. The description was made during mid-summer following the observation of representative plants two growing seasons following the year of propagation which were grown in an artificial soilless medium at West Grove, Pa.

Growth habit: Distinctly dwarf. The plants described above commonly possess a height of 12 to 15 inches and a breadth of 15 to 18 inches while the Emerald'N Gold variety commonly possesses a height of 18 to 21 inches and a breadth of 15 to 18 inches under the same growing conditions. The plant is suitable for growing as an attractive semi-prostrate ground cover.

Foliage:

*Type.*—Broadleaf evergreen; petioled; opposite.

*Shape.*—Slightly variable in shape. Mostly ovate with some leaves slightly more elliptic than Emerald'N Gold variety. Apex acute, base ovate. Margins serrate to serrate-crenate.

*Petioles.*—Approximately 3 to 5 mm. in length.

*Size.*—Mature leaves on current year's growth are smaller than those of the Emerald'N Gold variety. More specifically, the leaves of the present variety under the above growing conditions commonly measure approximately 1.7 to 2.7 cm. in length and approximately 1.2 to 1.7 cm. in breadth, while those of the Emerald'N Gold variety commonly measure approximately 1.9 to 3.2 cm. in length and 1.3 to 2.0 cm. in breadth. The leaves are expected to increase in size somewhat as the age of the plant increases as is common with other varieties of *Euonymus fortunei.*

*Color—upper surface.*—Immature leaves Green Group 137C edged with irregular band of Yellow Group 13B to 13D, and mature leaves Green Group 137A edged with irregular band of Yellow Group 11B.

*Color—under surface.*—Mature leaves Green Group 138A.

Flowers: None observed to date.

Hardiness: Good winter hardiness. The new variety has withstood temperatures of −20° F. when grown at Ipswich, Mass.

Disease and drought resistance: Good.

I claim:

1. A new and distinct variety of *Euonymus fortunei* which is a branch mutation of the Emerald'N Gold variety, substantially as herein shown and described, characterized particularly as to novelty by the unique combination of:

(a) a distinctly dwarf habit of growth rendering the plant suitable for use as a semi-prostrate ground cover, (b) smaller variegated leaves which when mature are dark green with light to medium yellow margins, (c) vigorous growth characteristics, (d) the ability to thrive under a wide range of climatic conditions, and (e) the ability to be sheared within prescribed limits or shaped to a specific form.

* * * * *